(12) United States Patent
Du et al.

(10) Patent No.: US 8,569,478 B2
(45) Date of Patent: Oct. 29, 2013

(54) MODIFIED 4'-NUCLEOSIDES AS ANTIVIRAL AGENTS

(75) Inventors: Jinfa Du, New Hope, PA (US); Phillip Furman, Princeton, NJ (US); Michael Joseph Sofia, Doylestown, PA (US)

(73) Assignee: Gilead Pharmasset LLC, Foster City, CA (US)

(*) Notice: Subject to any disclaimer, the term of this patent is extended or adjusted under 35 U.S.C. 154(b) by 878 days.

(21) Appl. No.: 12/067,995

(22) PCT Filed: Sep. 26, 2006

(86) PCT No.: PCT/US2006/037470
§ 371 (c)(1),
(2), (4) Date: Oct. 18, 2010

(87) PCT Pub. No.: WO2007/038507
PCT Pub. Date: Apr. 5, 2007

(65) Prior Publication Data
US 2011/0021454 A1    Jan. 27, 2011

Related U.S. Application Data

(60) Provisional application No. 60/720,388, filed on Sep. 26, 2005.

(51) Int. Cl.
C07H 19/04 (2006.01)
C07H 19/20 (2006.01)
C07H 19/10 (2006.01)
C07H 19/048 (2006.01)
C07H 19/22 (2006.01)
C07H 19/00 (2006.01)
C07D 239/00 (2006.01)
C07D 239/02 (2006.01)
C07D 473/00 (2006.01)
C07F 9/02 (2006.01)

(52) U.S. Cl.
USPC ..... 536/26.7; 536/26.8; 536/27.14; 536/28.2; 544/242; 544/243; 544/264

(58) Field of Classification Search
None
See application file for complete search history.

(56) References Cited

U.S. PATENT DOCUMENTS

| | | | |
|---|---|---|---|
| 5,041,449 A | 8/1991 | Belleau et al. | |
| 5,047,407 A | 9/1991 | Belleau et al. | |
| 5,149,794 A | 9/1992 | Yatvin et al. | |
| 5,194,654 A | 3/1993 | Hostetler et al. | |
| 5,223,263 A | 6/1993 | Hostetler et al. | |
| 5,256,641 A | 10/1993 | Yatvin et al. | |
| 5,411,947 A | 5/1995 | Hostetler et al. | |
| 5,432,273 A | 7/1995 | Liotta et al. | |
| 5,463,092 A | 10/1995 | Hostetler et al. | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,571,798 A | 11/1996 | Harmenberg et al. | |
| 5,817,799 A | 10/1998 | Marquez et al. | |
| 6,117,849 A | 9/2000 | Zimmermann et al. | |
| 6,403,568 B1 | 6/2002 | Ohrui et al. | |
| 6,949,522 B2 | 9/2005 | Otto et al. | |
| 2005/0009737 A1 | 1/2005 | Clark | |
| 2012/0232029 A1* | 9/2012 | Sofia et al. ..... | 514/46 |

FOREIGN PATENT DOCUMENTS

| | | |
|---|---|---|
| EP | 0337713 | 10/1989 |
| EP | 0350287 | 1/1990 |
| EP | 0382526 | 8/1990 |
| EP | 0457326 A1 | 11/1991 |
| EP | 0650371 | 11/2000 |
| JP | 62-103100 A | 5/1987 |
| JP | 2-500364 A | 2/1990 |
| JP | 4-226999 A | 8/1992 |
| WO | 88/03804 A2 | 6/1988 |
| WO | 89/02733 | 4/1989 |
| WO | 90/00555 | 1/1990 |
| WO | 91/16920 | 11/1991 |
| WO | 91/18914 | 12/1991 |
| WO | 91/19721 | 12/1991 |
| WO | 93/00910 | 1/1993 |
| WO | 93/17651 A2 | 9/1993 |
| WO | 94/26273 | 11/1994 |
| WO | 96/15132 | 5/1996 |
| WO | WO 00/69877 | 11/2000 |
| WO | 2005/011709 A1 | 2/2005 |

OTHER PUBLICATIONS

Hayakawa et al., "Potential of 4'-C-substituted nucleosides for the treatment of HIV-1." *Antiviral Chemistry and Chemotherapy* 15(2004): 169-187.
Office Action dated Aug. 23, 2008—Chilean Patent Application No. 2564-2006.
Office Action dated Apr. 15, 2009—Chilean Patent Application No. 2564-2006.
Office Action dated Aug. 17, 2009—Peru Patent Application No. 1186-2006.
Office Action dated Nov. 25, 2009—Eurasian Patent Application No. 200800932/28.
Office Action dated Jan. 26, 2011—Chinese Patent Application No. 200680042321.1.
European Patent Application No. 06825120.6 Extended European Search Report EPC Communication dated May 25, 2010.
Hrebabecky, et al., Collect. Czech. Chem. Commun., 1993, 58:7, 1668-1674.
Hrebabecky, et al., Collect. Czech. Chem. Commun., 1997, 62:7, 1114-1127.

(Continued)

*Primary Examiner* — Lawrence E Crane
(74) *Attorney, Agent, or Firm* — Fitzpatrick, Cella, Harper & Scinto

(57) ABSTRACT

Compounds, methods and compositions for treating a host infected with human immunodeficiency virus and hepatitis B virus comprising administering an effective amount of a described 4'-C-substituted β-D- and β-L-nucleoside or a pharmaceutically acceptable salt or prodrug thereof, are provided.

7 Claims, 3 Drawing Sheets

(56) References Cited

OTHER PUBLICATIONS

Maag, et al., J. Med. Chem., 1992, 35, 1440-1451.
Reihokainen, et al., Tetrahedron, 1998, 54:34, 10161-10166.
Sugimoto, et al., Bioorganic & Medicinal Chemistry Letters, 1999, 9:3, 385-388.
Examination Report dated Jul. 18, 2011—New Zealand Patent Application No. 567272.
International Search Report of PCT/US2006/037470 (WO2007/038507) mailed Jul. 12, 2007.
Written Opinion of PCT/US2006/037470 mailed Jul. 12, 2007.
International Preliminary Examination Report of PCT/US2006/037470 issued Mar. 26, 2008.
Written Opinion of Singapore Patent Application No. 200802368-1 dated Apr. 30, 2009.
Examination Report of Singapore Patent Application No. 200802368-1 dated Dec. 31, 2009.
Furman, P. A., et al., The Anti-Hepatitis B Virus Activities, Cytotoxicities, and Anabolic Profiles of the (−) and (+) Enantiomers of cis-5-Fluoro-1[2-(Hydroxymethyl)-1,3-Oxathiolan-5-yl]Cytosine, Antimicrobial Agents and Chemotherapy, 1992, 2686-2692.
Hostetler, K. Y., et al., Synthesis and Antiretroviral Activity of Phospholipid Analogs of Azidothymidine and Other Antiviral Nucleosides, J. Biol. Chem., 1990, 265, 6112-6117.
Hostetler, K. Y., et al., Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Dexoythymidine, Antimicrobial Agents and Chemotherapy, 1992, 36, 2025-2029.
Jones, R. J., et al., Minireview: nucleotide prodrugs, Antiviral Research, 1995, 27, 1-17.
Kucera, L. S., et al., Human Immunodeficiency Virus Type 1 (HIV-1) and Herpes Simplex Virus Type 2 (HSV-2) Can Coinfect and Simultaneously Replicate in the Same Human CD4+ Cell: Effect of Coinfection of Infectious HSV-2 and HIV-1 Replication, AIDS Research and Human Retroviruses, 1990, 6, 641-647.
Maillard, M., et al., Synthesis of 3'-Substituted-2',3'-Dideoxynucleoside Analogs as Potential Anti-AIDS Drugs, Tetrahedron Letters, 1989, 30, 1955-1958.
Nomura, M., et al., Nucleosides and Nucleotides. 185. Synthesis and Biological Activities of 4'α-C-Branched-Chain Sugar Pyrimidine Nucleosides, J. Med. Chem., 1999, 42, 2901-2908.
Norbeck, D. W., et al., (±)-Dioxolane-T ((±)-1-[(2β,4β)-2-(hydroxymethyl)-4-dioxolanyl]thymine): A New 2',3'-Dideoxynucleoside Prototype with in Vitro Activity Against HIV, Tetrahedron Letters, 1989, 30, 6263-6266.
Ohrui, H., et al., Syntheses of 4'-C-Ethynyl-β-D-arabino- and 4'-C-Ethynyl-2'-deoxy-β-D-ribo-pentofuranosylpyrimidines and -purines and Evaluation of Their Anti-HIV Activity, J. Med. Chem., 2000, 43, 4516-4525.
Otter, B. A., et al., Nucleosides. 108. Ribo-Xylo Interconversions of 6,5'-Cyclopyrimidine Nucleosides via Autoxidation and Retro-Aldol Reactions, J. Org. Chem., 1978, 43, 481-486.
Piantadosi, C., et al., Synthesis and Evaluation of Novel Ether Lipid Nucleoside Conjugates for Anti-HIV-1 Activity, J. Med. Chem., 1991, 34, 1408-1414.
Schinazi, R. F., et al., Selective Inhibition of Human Immunodeficiency Viruses by Racemates and Enantiomers of cis-5-Fluoro-1-[2-(Hydroxymethyl)-1,3-Oxathiolan-5-yl]Cytosine, Antimicrobial Agents and Chemotherapy, 1992, 2423-2431.
Siddiqui, M. A., et al., A 4'-C-Ethynyl-2',3'-Dideoxynucleoside Analogue Highlights the Role of the 3'-OH in Anti-HIV Active 4'-C-Ethynyl-2'-deoxy Nucleosides, J. Med. Chem., 2004, 47, 5041-5048.
Hrebabecky, H., et al., "Synthesis of 1-(3-Azido-2,3-dideoxy-4-C-hydroxymethyl-a-L-threo-Pentofuranosyl)thymine, 1-(2,3-Dideoxy-4-C-hydroxymethyl-a-L-glycero-pentofuranosyl)thymine and 1-(2,3-Dideoxy-4-C-hydroxymethyl-a-L-glycero-pent-2-enofuranosyl)thymine," Collect. Czech. Chem. Commun., vol. 58, pp. 409-420 (1993).
Hrebabecky, H., et al., "Synthesis of Carbocyclic 4'-C-Hydroxymethyl Analogues of Azidodeoxythymidine, Deoxythymidine, Deoxydidehydrothymidine and Thymidine Carba Analogue with Fused Oxetane Ring," Collect. Czech. Chem. Commun., vol. 65, pp. 395-406 (2000).
Kodama, E., et al., "4'-Ethynyl Nucleoside Analogs: Potent Inhibitors of Multidrug-Resistant Human Immunodeficiency Virus Variants in Vitro," Antimicrob. Agents Chemother., vol. 45, No. 5, pp. 1539-1546 (2001).
Office Action dated Mar. 31, 2011, issued in Malaysian Patent Application No. PI20080853 (3 pages).
Office Action mailed Mar. 29, 2012, issued in Philippines Patent Application No. 12008500725 (2 pages).
Office Action dated Nov. 14, 2011, issued in Australian Patent Application No. 2006294807 (3 pages).
Office Action mailed Jul. 10, 2012, issued in Japanese Patent Application No. 2008-533517 (4 pages).
Office Action mailed Nov. 27, 2012, issued in Japanese Patent Application No. 2008-533517 (2 pages).
Herdewijn, P. et al., "'—Substituted 2', 3'—Dideoxynucleoside Analogues as Potential Anti-HIV (HTLV-III/LAV) Agents, " *J. Med. Chem.*, vol. 30, No. 8, pp. 1270-1278 (1987).

* cited by examiner (I)  (II)

MODIFIED 4'-NUCLEOSIDES AS ANTIVIRAL AGENTS

CROSS-REFERENCE TO RELATED APPLICATION

This application claims priority to U.S. Provisional Patent Application No. 60/720,388, filed Sep. 26, 2005, the contents of which are incorporated by reference in its entirety herein.

INCORPORATION OF SEQUENCE LISTING

The Sequence Listing filed on Feb. 28, 2013, created/modified on Feb. 12, 2013, named 03956053400ST25.txt, having a size in bytes of 0.93 kB, is hereby incorporated by reference herein in its entirety.

FIELD OF THE INVENTION

This invention is in the area of pharmaceutical chemistry, and is in particular, a compound, method and composition for treating a host infected with human immunodeficiency virus (referred to below as "HIV"), hepatitis B virus (referred to below as "HBV"), or both HIV and HBV comprising administering an effective amount of a described β-D- and β-L-4'-C-substituted-3'-fluoro- and 3'-azido-3'-deoxynucleoside or a pharmaceutically acceptable salt or prodrug thereof.

BACKGROUND OF THE INVENTION

In 1981, acquired immune deficiency syndrome (AIDS) was identified as a disease that severely compromises the human immune system that almost without exception leads to death. In 1983, the etiological cause of AIDS was determined to be the HIV.

In 1985, it was reported that the synthetic nucleoside 3'-azido-3'-deoxythymidine (AZT) inhibits the replication of HIV. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside (Norbeck et al. 1989, *Tetrahedron Letters*, 30 (46) 6246, European Patent Application Publication No. 0 337 713, and U.S. Pat. No. 5,041,449).

U.S. Pat. No. 5,047,407 and European Patent Application Publication No. 0 382 526, disclose a number of racemic 2'-substituted-5'-substituted-1,3-oxathiolane nucleosides with antiviral activity, and specifically report that the racemic mixture (about the C4'-position) of the C1'-β isomer of 2-hydroxymethyl-5-(cytosin-1-yl)-1,3-oxathiolane (±)-BCH-189) has approximately the same activity against HIV as AZT, and no cellular toxicity at the tested levels. (±)-BCH-189 has also been found to inhibit the replication of AZT-resistant HIV isolates in vitro from patients who have been treated with AZT for longer than 36 weeks. The (−)-enantiomer of the isomer of BCH-189, known as 3TC, is highly potent against HIV and exhibits little toxicity. (−)-cis-2-hydroxymethyl-5-(5-fluorocytosin-1-yl)-1,3-oxathiolane ("FTC") also has potent HIV activity (Schinazi et al. 1992 *Antimicrob. Agent and Chemotherap,* 2423-2431).

Recently, 4'-C-substituted nucleosides have been reported to show potent anti-HIV activity (Siddiqui, M. A. et al. *J. Med. Chem.* 2004, 47, 5041-5048; Nomura, M. et al. *J. Med. Chem.* 1999, 42, 2901-2908).

Another virus that causes a serious human health problem is HBV. HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage that causes abdominal pain, jaundice, and elevated blood levels of certain enzymes. HBV can cause fulminant hepatitis, a rapidly progressive, often fatal form of the disease in which massive sections of the liver are destroyed.

In western industrialized countries, high-risk groups for HBV infection include those in contact with HBV carriers or their blood samples. The epidemiology of HBV is very similar to that of acquired immune deficiency syndrome, which accounts for why HBV infection is common among patients with AIDS or AIDS-related complex. However, HBV is more contagious than HIV. Both FTC and 3TC exhibit activity against HBV (Furman et al. 1992 *Antimicrobial Agents and Chemotherapy,* 2686-2692).

A human serum-derived vaccine has been developed to immunize patients against HBV. While it has been found effective, production of the vaccine is troublesome because the supply of human serum from chronic carriers is limited, and the purification procedure is long and expensive. Further, each batch of vaccine prepared from different serum must be tested in chimpanzees to ensure safety. Vaccines have also been produced through genetic engineering. Daily treatments with α-interferon, a genetically engineered protein, have also shown promise.

In light of the fact that acquired immune deficiency syndrome, AIDS-related complex, and hepatitis B virus have reached epidemic levels worldwide, and have tragic effects on the infected patient, there remains a strong need to provide new effective pharmaceutical agents to treat these diseases and that have low toxicity to the host.

SUMMARY OF THE INVENTION

The present invention discloses compounds, their synthesis, methods and compositions for treating a host infected with HIV, HBV, or both HIV and HBV comprising administering an effective amount of a described β-D- and β-L-4'-C-substituted-3'-fluoro- and 3'-azido-3'-deoxynucleoside or a pharmaceutically acceptable salt or prodrug thereof.

DETAILED DESCRIPTION OF THE INVENTION

Figure 1:
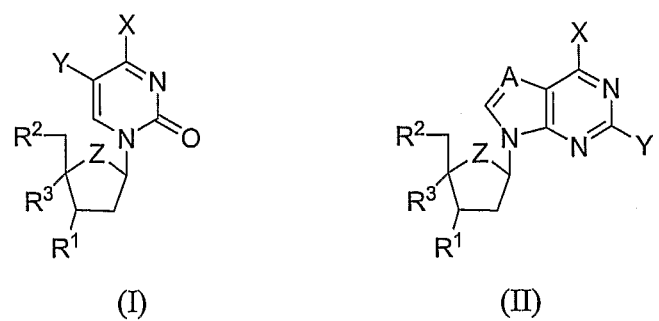
FIG. 1 represents chemical structures of modified 4'-nucleosides as antiviral agents.

The present invention relates to a method and composition for treating HIV, HBV, or both HIV and HBV infections in a host comprising administering an effective amount of a described β-D- and β-L-4'-C-substituted 3'-fluoro- and 3'-azido-3'-dideoxynucleosides or their pharmaceutically acceptable salts and prodrugs and thereof.

More specifically, a first aspect of the present invention is directed to compounds, methods and compositions for treating a host infected with HIV, HBV, or both HIV and HBV comprising administering an effective amount of a described β-D- and β-L-nucleoside of the formulas I and II or a pharmaceutically acceptable salt or prodrug thereof.

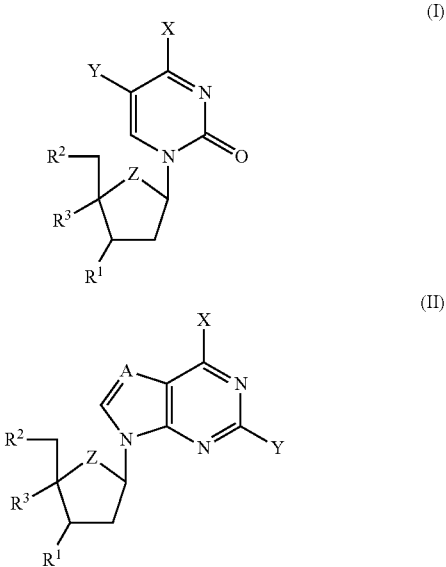

wherein:
X is hydrogen, halogen (F, Cl, Br, I), $NH_2$, $NHR^4$, $NR^4R^5$, NHOH, $NHOR^4$, $NHNH_2$, $NR^4NH_2$, $NHNHR^4$, SH, $SR^4$, $S(O)R^4$, $S(O)_2R^4$, OH, $OR^4$, $N_3$, CN, or $CF_3$.

Y is hydrogen, halogen (F, Cl, Br, I), $NH_2$, $NHR^4$, $NR^4R^5$, NHOH, $NHOR^4$, $NHNH_2$, $NR^4NH_2$, $NHNHR^4$, SH, $SR^4$, $S(O)R^4$, $S(O)_2R^4$, OH, $OR^4$, $N_3$, CN, $CF_3$, hydroxymethyl, methyl, optionally substituted or unsubstituted ethyl, optionally substituted or unsubstituted vinyl, optionally substituted or unsubstituted 2-bromovinyl, optionally substituted or unsubstituted ethynyl;

$R^1$ is F or $N_3$;

$R^2$ is OH, $OR^4$, $OC(O)R^4$, $OP_vO_{3v}M_xR^4_yR^5_z$, $P_vO_{3v}M_xR^4_yR^5_z$, $OCH_2OP_vO_{3v}M_xR^4_yR^5_z$, $OP(O)(OQ)_a$ $(NHR^4)_b$, SH, $SR^4$, $S(O)R^4$, $S(O)_2R^4$, $SC(O)R^4$, $NH_2$, $NHC(O)R^4$, $NHR^4$, $NR^4R^5$, NHOH, $NHOR^4$, $NHNH_2$, $NR^4NH_2$, or $NHNHR^4$;

$R^3$ is F, cyano, azido, ethynyl, chlorovinyl, fluorovinyl, alkyl ($C_{1-6}$), one to three halogen substituted alkyl ($C_{1-6}$), alkenyl ($C_{1-6}$) or alkynyl ($C_{1-6}$) with the proviso that when $R^1$ is $N_3$, $R^3$ is not hydroxymethyl;

Z is O, S, $CH_2$ or $C=CH_2$;

A is N, CH, or CF; and $R^4$ and $R^5$ are the same or different and are lower alkyl, lower alkenyl, acyl of carbon 1-17, aryl, or aralkyl, such as unsubstituted or substituted phenyl or benzyl M is at least one member selected from the group consisting of $H^+$, $Na^+$, and $K^+$;

v has a value of 1, 2, or 3;

x, y, and z are independent of each other and have a value of 0, 1, 2, 3, or 4; and a has a value of 0 or 1, b has a value of 1 or 2, and Q is M or $R^4$.

A second aspect of the present invention is directed to an intermediate of the formula:

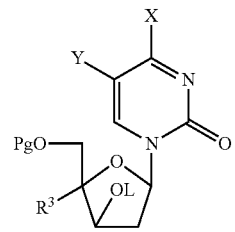

wherein

X is hydrogen, F, Cl, Br, I, $NH_2$, $NHR^4$, $NR^4R^5$, NHOH, $NHOR^4$, $NHNH_2$, $NR^4NH_2$, $NHNHR^4$, SH, $SR^4$, $S(O)R^4$, $S(O)_2R^4$, OH, $OR^4$, $N_3$, CN, or $CF_3$;

Y is hydrogen, F, Cl, Br, I, $NH_2$, $NHR^4$, $NR^4R^5$, NHOH, $NHOR^4$, $NHNH_2$, $NR^4NH_2$, $NHNHR^4$, SH, $SR^4$, $S(O)R^4$, $S(O)_2R^4$, OH, $OR^4$, $N_3$, CN, $CF_3$, hydroxymethyl, methyl, optionally substituted or unsubstituted ethyl, optionally substituted or unsubstituted vinyl, optionally substituted or unsubstituted 2-bromovinyl, optionally substituted or unsubstituted ethynyl;

$R^3$ is F, cyano, azido, ethynyl, chlorovinyl, fluorovinyl, alkyl ($C_{1-6}$), one to three halogen substituted alkyl ($C_{1-6}$), alkenyl ($C_{1-6}$) or alkynyl ($C_{1-6}$) with the proviso that when $R^1$ is $N_3$, $R^3$ is not hydroxymethyl;

Pg is a hydroxyl protecting group that includes, but is not limited to trityl, dimethoxytrityl, and t-butyl-silyl;

L is a leaving group that includes, but is not limited to a sulfonyl, a trifluorosulfonyl, an unsubstituted sulfonate, a substituted sulfonate, an unsubstituted carbonate, and a substituted carbonate; and $R^4$ and $R^5$ are the same or different and are lower alkyl, lower alkenyl, acyl of carbon 1-17, aryl, or aralkyl.

A third aspect of the present invention is directed to a process for the preparation of an intermediate disclosed in the second aspect of the present invention, which comprises:

(a): selectively protecting a 5'-OH with a protecting group, Pg, to form a 5'-OPg group;

(b): activating a 3'-OH with a leaving group, L, to form a 3'-OL group;

(c): reacting a 3'-C with a hydroxide base in order to convert the 3'-C position from a ribo- to a xylo-configuration;

(d): activating a 3'-OH having a xylo-configuration with a leaving group, L, to form a 3'-OL group;

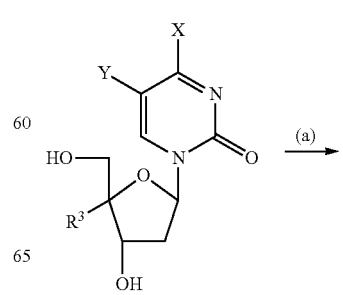

(a)

-continued

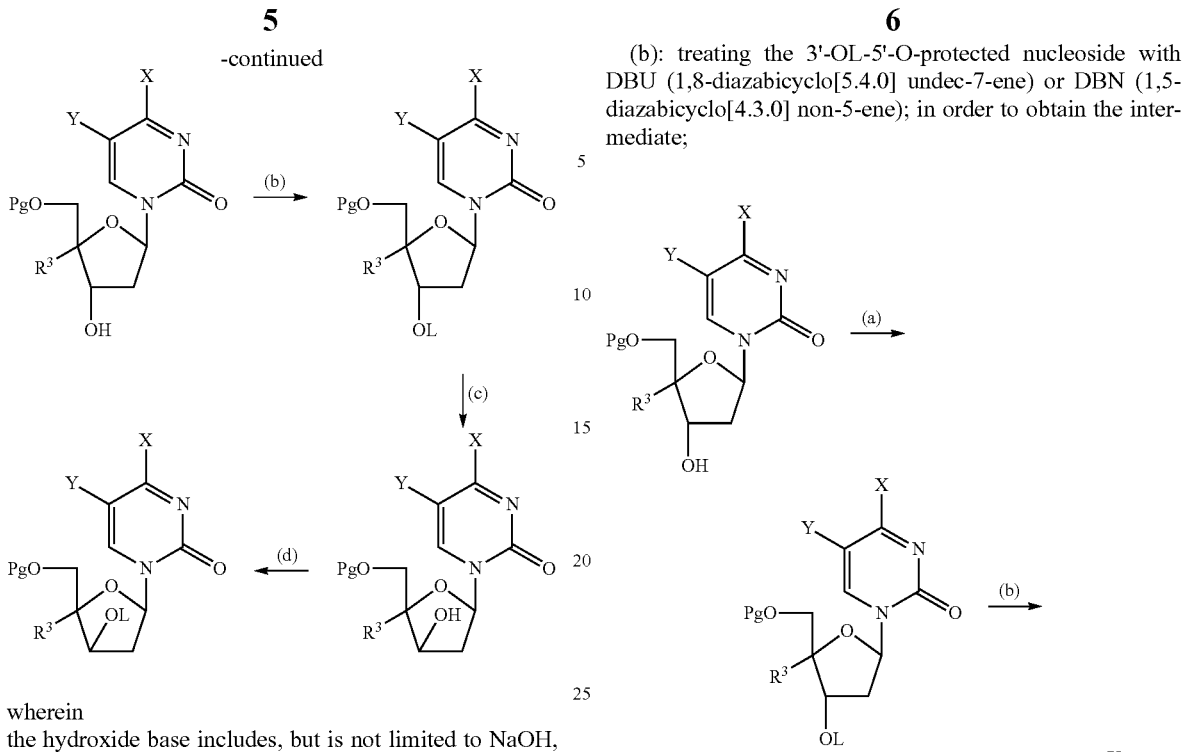

wherein
the hydroxide base includes, but is not limited to NaOH, KOH, and $R^4_4NOH$, and mixtures thereof.

A fourth aspect of the present invention is directed to an intermediate of formula:

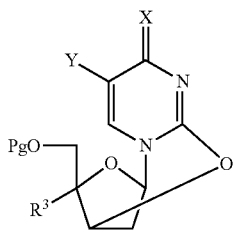

wherein
X is hydrogen, F, Cl, Br, I, $NH_2$, $NHR^4$, $NR^4R^5$, NHOH, $NHOR^4$, $NHNH_2$, $NR^4NH_2$, $NHNHR^4$, SH, $SR^4$, $S(O)R^4$, $S(O)_2R^4$, OH, $OR^4$, $N_3$, CN, or $CF_3$;
Y is hydrogen, F, Cl, Br, I, $NH_2$, $NHR^4$, $NR^4R^5$, NHOH, $NHOR^4$, $NHNH_2$, $NR^4NH_2$, $NHNHR^4$, SH, $SR^4$, $S(O)R^4$, $S(O)_2R^4$, OH, $OR^4$, $N_3$, CN, $CF_3$, hydroxymethyl, methyl, optionally substituted or unsubstituted ethyl, optionally substituted or unsubstituted vinyl, optionally substituted or unsubstituted 2-bromovinyl, optionally substituted or unsubstituted ethynyl;
$R^3$ is F, cyano, azido, ethynyl, chlorovinyl, fluorovinyl, alkyl ($C_{1-6}$), one to three halogen substituted alkyl ($C_{1-6}$), alkenyl ($C_{1-6}$) or alkynyl ($C_{1-6}$) with the proviso that when $R^1$ is $N_3$, $R^3$ is not hydroxymethyl;
Pg is a hydroxyl protecting group that includes, but is not limited to, trityl, dimethoxytrityl, and t-butyl-silyl; and
$R^4$ and $R^5$ are the same or different and are lower alkyl, lower alkenyl, acyl of carbon 1-17, aryl, or aralkyl.

A fifth aspect of the present invention is directed to a process for the preparation of the intermediate disclosed in the fourth aspect of the present invention, which comprises:
(a): activating a 3'-OH of a 5'-O-protected nucleoside with a leaving group, L; to form a 3'-OL-5'-O-protected nucleoside group; followed by (b): treating the 3'-OL-5'-O-protected nucleoside with DBU (1,8-diazabicyclo[5.4.0] undec-7-ene) or DBN (1,5-diazabicyclo[4.3.0] non-5-ene); in order to obtain the intermediate;

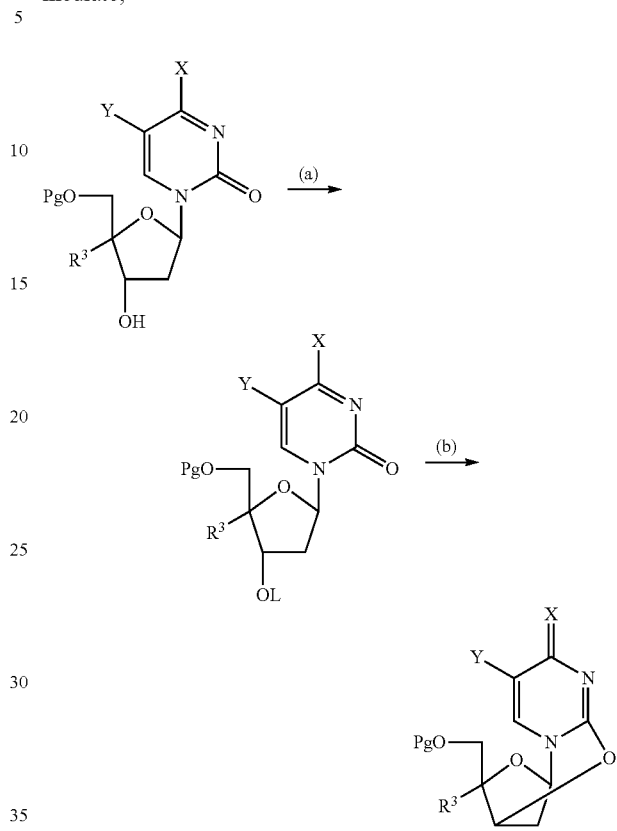

wherein L includes, but is not limited to a sulfonyl, a trifluorosulfonyl, a substituted sulfonate, an unsubstituted sulfonate, an unsubstituted carbonate, and a substituted carbonate.

Various embodiments of the invention are now described in detail. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The disclosed compounds or their pharmaceutically acceptable derivatives or salts or pharmaceutically acceptable formulations containing these compounds are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

The compounds and their pharmaceutically acceptable derivatives or pharmaceutically acceptable formulations containing the compound or their derivatives are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

The compounds can be converted into a pharmaceutically acceptable ester by reaction with an appropriate esterifying agent, for example, an acid halide or anhydride. The compounds or their pharmaceutically acceptable derivative can be converted into a pharmaceutically acceptable salt thereof in a conventional manner, for example, by treatment with an appropriate base. The ester or salt of the compound can be converted into the parent compound, for example, by hydrolysis.

The term "independently" is used herein to indicate that the variable, which is independently applied, varies independently from application to application. Thus, in a compound such as $R^aXYR^a$, wherein $R^a$ is "independently carbon or nitrogen," both $R^a$ can be carbon, both $R^a$ can be nitrogen, or one $R^a$ can be carbon and the other $R^a$ nitrogen.

As used herein, the term "enantiomerically pure" refers to a nucleoside composition that comprises at least approximately 95%, and preferably approximately 97%, 98%, 99% or 100% of a single enantiomer of that nucleoside.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of the non-designated enantiomer of that nucleoside.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in Greene et al. 1991, *Protective Groups in Organic Synthesis*, John Wiley & Sons, $2^{nd}$ Edition, hereby incorporated by reference.

The term "lower alkyl," as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "lower alkenyl," as used herein, and unless otherwise specified, refers to a $C_2$ to $C_4$ unsaturated straight or branched alkenyl group, including both substituted and unsubstituted forms. Unless otherwise specifically stated in this application, when alkenyl is a suitable moiety, lower alkenyl is preferred. Similarly, when alkenyl or lower alkenyl is a suitable moiety, unsubstituted alkenyl or lower alkenyl is preferred.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene et al. 1991, *Protective Groups in Organic Synthesis*, John Wiley & Sons, $2^{nd}$ Edition.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

The term "lower acyl" refers to an acyl group in which the non-carbonyl moiety is lower alkyl.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates and humans. In most animal applications of the present invention, the host is a human patient. Veterinary applications, in certain indications, however, are clearly anticipated by the present invention.

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

1. Non-Limiting Example of the Synthesis of 4'-C-ethynyl-3'-fluoro- and 3'-azidothymidines (see FIG. 2)

Treatment of thymidine with 2.2-2.5 moles of t-butyldimethylsilyl chloride in methylene chloride in the presence of imidazole followed by selective deprotection of 5'-O-silyl group in 80% acetic acid in the presence of trifluoroacetic acid gave compound 2. Oxidation of 2 with DCC in DMSO in the presence of pyridinium trifluoroacetate gave an aldehyde 3 after silica gel column chromatographic purification in excellent yield. Treatment of compound 3 with aqueous formaldehyde in a mixture of 1,4-dioxane and water in the presence of 2N NaOH followed by reduction of the resulting intermediate by $NaBH_4$ provided diol 4. Selective protection of diol 4 with dimethoxytrityl chloride in pyridine afforded compound 5. Treatment of compound 5 with t-butyldiphenylsilyl chloride in methylene chloride in the presence of imidazole followed by detritylation in 80% acetic acid gave compound 6. Oxidation of alcohol 6 with DCC in DMSO in the presence of pyridinium trifluoroacetate provided compound 7. Reaction of compound 7 with chloromethylene Wittig reagent followed by elimination by treatment with butyllithium afforded 4'-C-ethynyl nucleoside 8. Treatment of 8 with tetrabutylammonium fluoride in THF gave 4'-C-ethynyl-thymidine 9. Treatment of 9 with DMTrCl in pyridine gave compound 10. Compound 10 was converted to 11 by treatment with MsCl followed by NaOH in EtOH. Treatment of compound 11 with DAST in methylene chloride at refluxing temperature in the presence of pyridine provided 3'-fluoronucleoside (12, X=F). 3'-Azidonucleoside (12, X=$N_3$) was obtained by treatment of 11 with mesyl chloride in methylene chloride in the presence of triethylamine followed $NaN_3$ in DMF. The final products, 4'-C-ethynyl-FLT (Ia, $R^1$=F, $R^2$=OH, $R^3$=ethynyl) and 4'-C-ethynyl-AZT (Ia, $R^1$=$N_3$, $R^2$=OH, $R^3$=ethynyl) are obtained by treatment of 12 with 80% acetic acid.

Alternatively, reaction of 10 with MsCl in the presence of base, such as triethylamine and the like, followed by treatment of the resulting mesylate with base, such as DBU or DBN or the like, gave intermediate 11'. Treatment of 11' with $NaN_3$ or tetrabutylammonium fluoride (TBAF) also provided the same intermediate 12 with X=$N_3$ or X=F, respectively, as disclosed in Maillard, M. et al. Tetrahedron Lett. 1989, 30, 1955-1958. The inventors, by way of example, do not intend to be limited to thymidine mentioned above, and hereby incorporate by reference the disclosures of U.S. Pat. No. 6,949,522; U.S. Pat. No. 6,403,568; and US 2005/0009737, each of which discloses examples of purines and pyrimidines that are contemplated.

Figure 3:
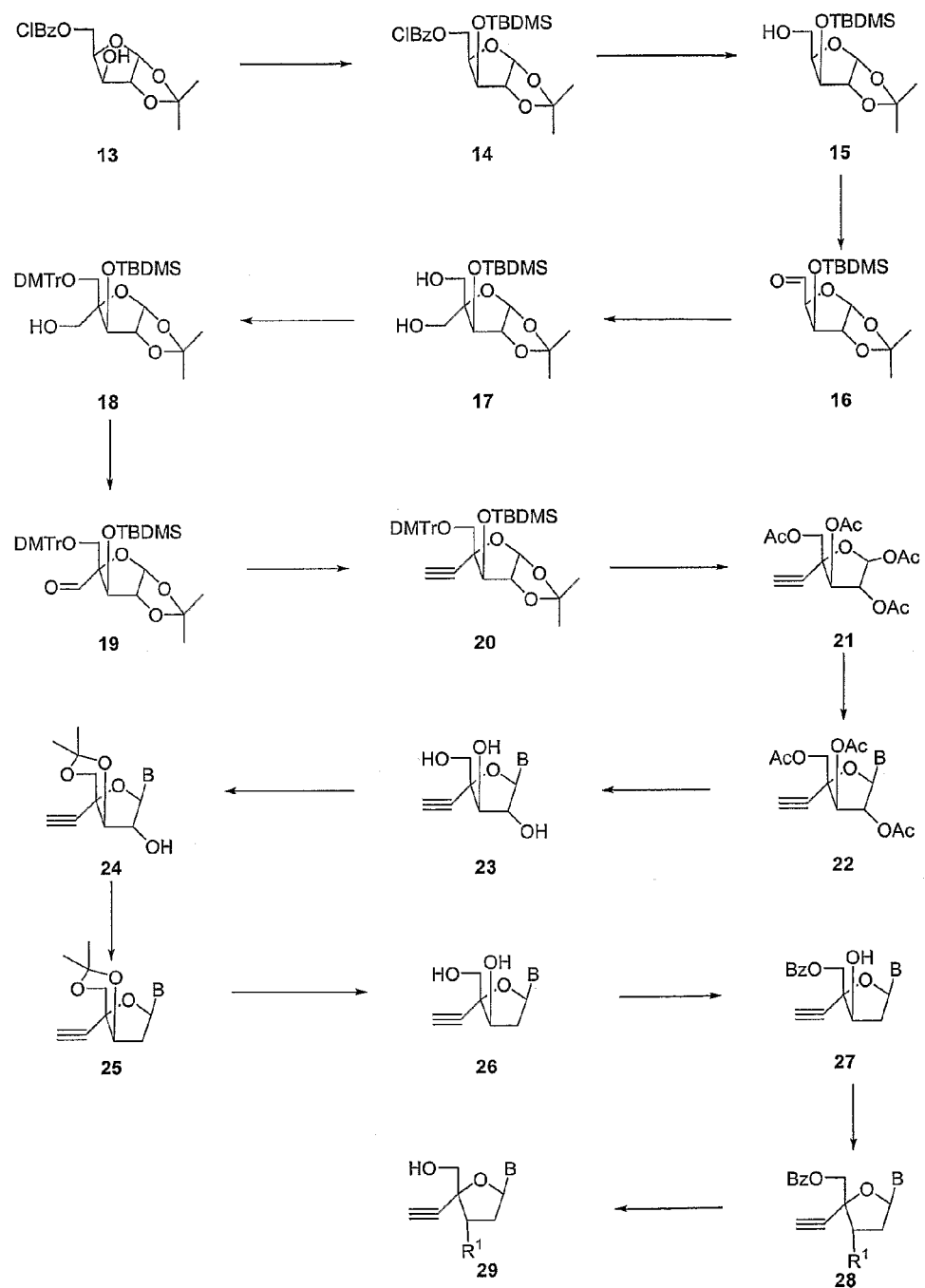
FIG. 3 is a nonlimiting illustrative example of the synthesis of 4'-C-ethynyl-3'-fluoro-2',3'-dideoxynucleosides (29, $R^1$=F) and 3'-azido-2',3'-dideoxynucleosides (29, $R^1$=$N_3$).

2. Non-limiting Example of the Synthesis 4'-C-ethynyl-3'-fluoro- and 3'-azido-2',3'-dideoxynucleosides (see FIG. 3)

Treatment of compound 13 with t-butyldimethylsilyl chloride in methylene chloride in the presence of imidazole followed by removal of chlorobenzoyl protecting group with methanolic ammonia gave compound 15. Oxidation of compound 15 with DCC in DMSO in the presence of pyridinium trifluoroacetate provided an aldehyde 16 after silica gel column chromatographic purification. Treatment of compound 16 with aqueous formaldehyde in a mixture of 1,4-dioxane and water in the presence of 2N NaOH followed by reduction of the resulting intermediate with $NaBH_4$ afforded diol 17. Selective protection with DMTCl followed by oxidation with DCC in DMSO in the presence of pyridinium trifluoroacetate gave an aldehyde 19. Reaction of 19 with chloromethylene Wittig reagent followed by elimination in the presence of butyllithium provided 4'-C-ethynyl-xylofuranoside 20. Acetolysis of 20 with acetic anhydride in acetic acid in the presence of concentrated sulfuric acid afforded tetraacetate 21. Coupling of 21 with silylated bases in the presence of Lewis acid, such as TMSOTf or $SnCl_4$, followed by deprotection with methanolic ammonia provided 4'-C-ethynyl-xylofuranosyl-nucleosides 23. Treatment of compound 23 with acetone in the presence of catalytic amount of HCl gave compound 24. Compound 24 was subjected to Barton deoxygenation to yield 2'-deoxynucleosides 25. Deisopropylenation of 25 with 80% acetic acid followed by selective protection with BzCl in pyridine provided nucleosides 27. Treatment of compound 27 with DAST in methylene chloride at reflux temperature followed by deprotection with methanolic ammonia provided the final 4'-C-ethynyl-nucleosides (29, $R^1$=F). Treatment of 27 with methanesulfonyl chloride in methylene chloride in the presence of triethylamine followed by reaction of the resulting mesylate with $NaN_3$ in DMF gave 4'-C-ethynyl-nucleosides (29, $R^1$=$N_3$).

The synthetic schemes disclosed above provide for the following contemplated compounds that include, but are not limited to: a 4'-C-substituted-3'-fluoro-2',3'-dideoxynucleoside, a 4'-C-substituted-3'-azido-2',3'-dideoxynucleoside, a 4'-C-ethynyl-3'-fluoro-2',3'-dideoxynucleoside, a 4'-C-ethynyl-3'-azido-2',3'-dideoxynucleoside, a 4'-C-ethynyl-3'-fluoro-3'-deoxythymidine, and a 4'-C-ethynyl-3'-azido-3'-deoxythymidine.

The antivirally active nucleosides can be administered as any derivative that upon administration to the host recipient is capable of providing, directly or indirectly, the parent compound, or that exhibits activity itself. Nonlimiting examples include the pharmaceutically acceptable salts (alternatively referred to as "physiologically acceptable salts") and prodrugs.

Modifications of the active compound, specifically at the $N^4$ and 5'-O positions, can affect the bioavailability and rate of metabolism of the active species, thus providing control over the delivery of the active species. Further, the modifications can affect the antiviral activity of the compound, in some cases increasing the activity over the parent compound. This can easily be assessed by preparing the derivative and testing its antiviral activity according to the methods described herein, or other methods known to those skilled in the art.

The inventors of the present application also contemplate the use of an antivirally effective amount of any of the compounds disclosed herein or a pharmaceutically acceptable salt or prodrug thereof.

Pharmaceutically Acceptable Salts and Prodrugs

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound.

Pharmaceutically acceptable salts include those derived from pharmaceutically acceptable inorganic or organic bases and acids. In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, but not limited to, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting with a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically acceptable prodrugs refer to a compound that is metabolized in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

Any of the nucleosides described herein can be administered as a nucleotide prodrug to increase the activity, bioavailability, stability or otherwise alter the properties of the nucleoside. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

In various embodiments, prodrugs of the nucleoside derivatives, in which $R^1$ is F or $N_3$, described herein involve substitution at the 5' carbon ($R^2$) with: OH, $OR^4$, $OC(O)R^4$, $OP_vO_{3v}$, $M_xR^4_yR^5_z$, $P_vO_{3v}M_xR^4_yR^5_z$, $OCH_2P_vO_3M_xR^4_yR^5_z$, $OP(O)(OQ)_a(NHR^4)_b$, SH, $SR^4$, $SC(O)R^4$, $NH_2$, $NHC(O)R^4$, $NHR^4$, $NR^4R^5$, NHOH, $NHOR^4$, $NHNH_2$, $NR^4NH_2$, or $NHNHR^4$. $R^4$ and $R^5$ are the same or different and are lower alkyl, lower alkenyl, acyl of carbon 1-17, aryl, or aralkyl, such as unsubstituted or substituted phenyl or benzyl; M is at least one member selected from the group consisting of $H^+$, $Na^+$, and $K^+$; v has a value of 1, 2, or 3; x, y, and z are independent of each other and have a value of 0, 1, 2, 3, or 4; and a has a value of 0 or 1, b has a value of 1 or 2, and Q is M or $R^4$. The inventors appreciate that one of ordinary skill should be able to recognize that for the phosphates and phosphonates represented above, that when v is 1 the sum of x, y, and z is 2; when v is 2, the sum of x, y, and z is 3; and when v is 3, the sum of x, y, and z is 4.

The phosphates ($OP_vO_{3v}M_xR^4_yR^5_z$) comprise mono- (v=1), di- (v=2), and tri-phosphates (v=3) in acid, salt, or ester form, including combinations thereof. In the instance where v=2, the nucleoside is substituted at the 5'-C position by an $R^2$ having the following structure: $OP_2O_6M_xR^4_yR^5_z$, where x, y, and z have the meanings as defined above. One of ordinary skill will recognize that the pure acid form is represented by ($OP_2O_6H_3$); the pure salt form is represented by ($OP_2O_6M_3$, M=$Na^+$, $K^+$, or both $Na^+$ and $K^+$); and the pure ester form is represented by ($OP_2O_6R^4_yR^5_z$, in which, as noted above, $R^4$ and $R^5$ may be the same or different and that if different the sum of y and z does not exceed 3). Of course, it is also contemplated that phosphates may be in a mixed form. By a mixed form it is understood that the phosphate moiety may be an acid (when M=$H^+$), a salt (when M=$Na^+$ or $K^+$; or even $Ca^{2+}$), or an ester (in which either or both of y and z of $R^4$ and $R^5$ have non-zero values). Not to be limited by way of example, the following structures represent preferred examples of contemplated phosphates: $OPO_3H_2$, $OP_2O_6H_3$, $OP_3O_9H_4$, $OPO_3Na_2$, $OPO_3R^4R^5$, $OP_2O_6Na_3$, $OP_2O_6R^4_2R^5$, $OP_3O_9Na_4$, $OP_3O_9R^4_3R^5$, $PO_3H_2$, $P_2O_6H_3$, $P_3O_9H_4$, $PO_3Na_2$.

It is contemplated that $R^4$, $R^5$, or both $R^4$ and $R^5$ can have the following formula: $R^6C(O)OR^7$, in which $R^6$ is an alkyl, such as a lower alkyl, and $R^7$ is a lower alkylene (such as methylene, ethylene, propylene, and butylene, which may be unsubstituted or substituted (with a hydroxyalkyl, alkoxyalkyl, or haloalkyl), with the proviso that $R^7$ is bound to the phosphoester oxygen. Not to be limited by example, but is contemplated that the nucleoside is substituted at the 5'-C position by a moiety having the following structure: $OP(O)[OCH_2OC(O)C(CH_3)_3]_2$.

The union of the 5'-C position with the P of a moiety ($P_vO_{3v}M_xR^4_yR^5_z$) gives rise to a mono- (v=1), di- (v=2), or tri-phosphonates (v=3), having acid, salt, or ester forms, including combinations thereof. In the instance where v=1, the nucleoside is substituted at the 5'-C position by a $R^2$ represented by $(PO_3M_xR^4_yR^5_z)$. One of ordinary skill will recognize that the pure acid form is represented by $(PO_3H_2)$; the pure salt form is represented by $(OPO_3M_2, M=Na^+, K^+,$ or both $Na^+$ and $K^+$); and the pure ester form is represented by $(OPO_3R^4_yR^5_z$, in which, as noted above, $R^4$ and $R^5$ may be the same or different and that if different the sum of y and z does not exceed 2). Of course, it is also contemplated that phosphonates may be in a mixed form. By a mixed form it is understood that the phosphonate moiety may be an acid (when $M=H^+$), a salt (when $M=Na^+$ or $K^+$; or even $Ca^{2+}$), or an ester (in which either or both of y and z of $R^4$ and $R^5$ have none zero values). Not to be limited by way of example, the following preferred examples of $R^2$ substituents give rise to contemplated phoshonates: $PO_3H_2$, $P_2O_6H_3$, $P_3O_9H_4$, $PO_3Na_2$, $P_2O_6Na_3$, $P_3O_9Na_4$, $PO_3R^4R^5$, $P_2O_6R^4_2R^5$, $P_3O_9R^4_3R^5$.

Additionally, the inventors contemplate prodrugs of the nucleoside derivatives that involve substitution at the 5' carbon with phosphoramidates $(OP(O)(OQ)_a(NHR^4)_b)$, in which a has a value of 0 or 1, b has a value of 1 or 2, and Q is M or $R^4$.

The active nucleoside can also be provided as a 5'-phosphoether lipid or a 5'-ether lipid, as disclosed in the following references, which are incorporated by reference herein: Kucera, L. S., et al. 1990. *AIDS Rex Hum. Retro Viruses.* 6:491-501; Piantadosi, G., et al. 1991. *J. Med. Chem.* 34:1408.1414; Hostetler, K. Y., et al. 1992, *Antim. Agents Chemother.* 36:2025.2029; Hosetler, K. Y., et al.1990, *J Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794; 5,194,654; 5,223,263; 5,256,641; 5,411,947; 5,463,092; 5,543,389; 5,543,390; 5,543,391; and 5,554,728, all of which are incorporated herein by reference. Foreign patent applications that disclose lipophilic substituents that can be attached to the nucleosides of the present invention, or lipophilic preparations, include WO 89/02733, WO 90100555, WO 91/16920, WO 91/18914, WO 93/00910, WO 94/26273, WO 96/15132, EP 0 350 287, EP 93917054.4, and WO 91/19721.

Pharmaceutical Compositions

Pharmaceutical compositions based upon a nucleoside compound of formula (I) and (II) or its pharmaceutically acceptable salt or prodrug can be prepared in a therapeutically effective amount for treating an HBV or HIV viral infection or abnormal cellular proliferation, optionally in combination with a pharmaceutically acceptable additive, carrier or excipient. The therapeutically effective amount may vary with the infection or condition to be treated, its severity, the treatment regimen to be employed, the pharmacokinetics of the agent used, as well as the patient treated.

In one aspect according to the present invention, the compound is formulated preferably in admixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity.

In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of HBV and HIV viral infections.

The amount of compound included within therapeutically active formulations, according to the present invention, is an effective amount for treating the infection or condition, in preferred embodiments, an HBV or an HIV viral infection. In general, a therapeutically effective amount of the present compound in pharmaceutical dosage form usually ranges from about 0.1 mg/kg to about 100 mg/kg or more and all values and sub-ranges therebetween, depending upon the compound used, the condition or infection treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

In addition, compounds according to the present invention can be administered in combination or alternation with one or more antiviral, anti-HBV, anti-HIV or interferon, anti-bacterial agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

Combination or Alternation Therapy

In another embodiment, for the treatment, inhibition, prevention and/or prophylaxis of viral infection, the active compound or its derivative or salt can be administered in combination or alternation with another antiviral agent. In general, in combination therapy, effective dosages of two or more agents are administered together, whereas during alternation therapy, an effective dosage of each agent is administered serially. The dosage will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include, but are not limited to, acyclovir (ACV), ganciclovir (GCV or DHPG) and its prodrugs (e.g. valyl-ganciclovir), E-5-(2-bromovinyl)-2-deoxyuridine (BVDU), (E)-5-vinyl-1-β-D-arabonosyluracil (VaraU), (E)-5-(2-bromovinyl)-1-β-D-arabinosyluracil (BV-araU), 1-(2-deoxy-2-fluoro-β-D-arabinosyl)-5-iodocytosine (D-FIAC), 1-(2-deoxy-2-fluoro-β-L-arabinosyl)-5-methyluracil (L-FMAU), (S)-9-(3-hydroxy-2-phosphonylmethoxypropyl)adenine[(S)—HPMPA], (S)-9-(3-hydroxy-2-phosphonylmethoxypropyl)-2,6-diaminopurine[(S)—HPMPDAP], (S)-1-(3-hydroxy-2-phosphonyl-methoxypropyl)cytosine[(S)—HPMPC, or cidofivir], and (2S,4S)-1-[2-(hydroxymethyl)-1,3-dioxolan-4-yl]-5-iodouracil (L-5-IoddU), FTC, entecavir, interferon-α, pegelated interferon-α, lamivudine (3TC), LdT (or its prodrug), LdC (or its prodrug), and adefovir, protease inhibitors (Agenerase, Crixivan, Fortovase, Invirase, Kaletra, Lexiva, Norvir, Reyataz, Aptivus and Viracept), and non nucleoside reverse transcriptase inhibitors (Rescriptor, Sustiva and Viramune).

Further nonlimiting examples of antiviral agents that can be used in combination with the compounds disclosed herein include, but are not limited to, the (−)-enantiomer of 2-hydroxymethyl-5-(5-fluorocytosin-1-yl)-1,3-oxathiolane [(−)—FTC); the (−)-enantiomer of 2-hydroxymethyl-5-(cytosin-1-yl)-1,3-oxathiolane (3TC); carbovir, acyclovir, interferon, famciclovir, penciclovir, AZT, DDI, DDC, L-(−)—FMAU, and D4T.

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, they should in no way, regardless, whether they are right or wrong, limit the scope of the invention so long as data are processed, sampled, converted, or the like according to the invention without regard for any particular theory or scheme of action.

EXAMPLES

Example 1

Preparation of 4'-C-ethynylthymidine

4'-C-Ethynylthymidine is prepared according to literature methods. (Nomura, M et al. *J. Med. Chem.* 1999, 42, 2901-2908; and Ohrui, H. et al. *J. Med. Chem.* 2000, 43, 4516-4525).

Example 2

Figure 2:
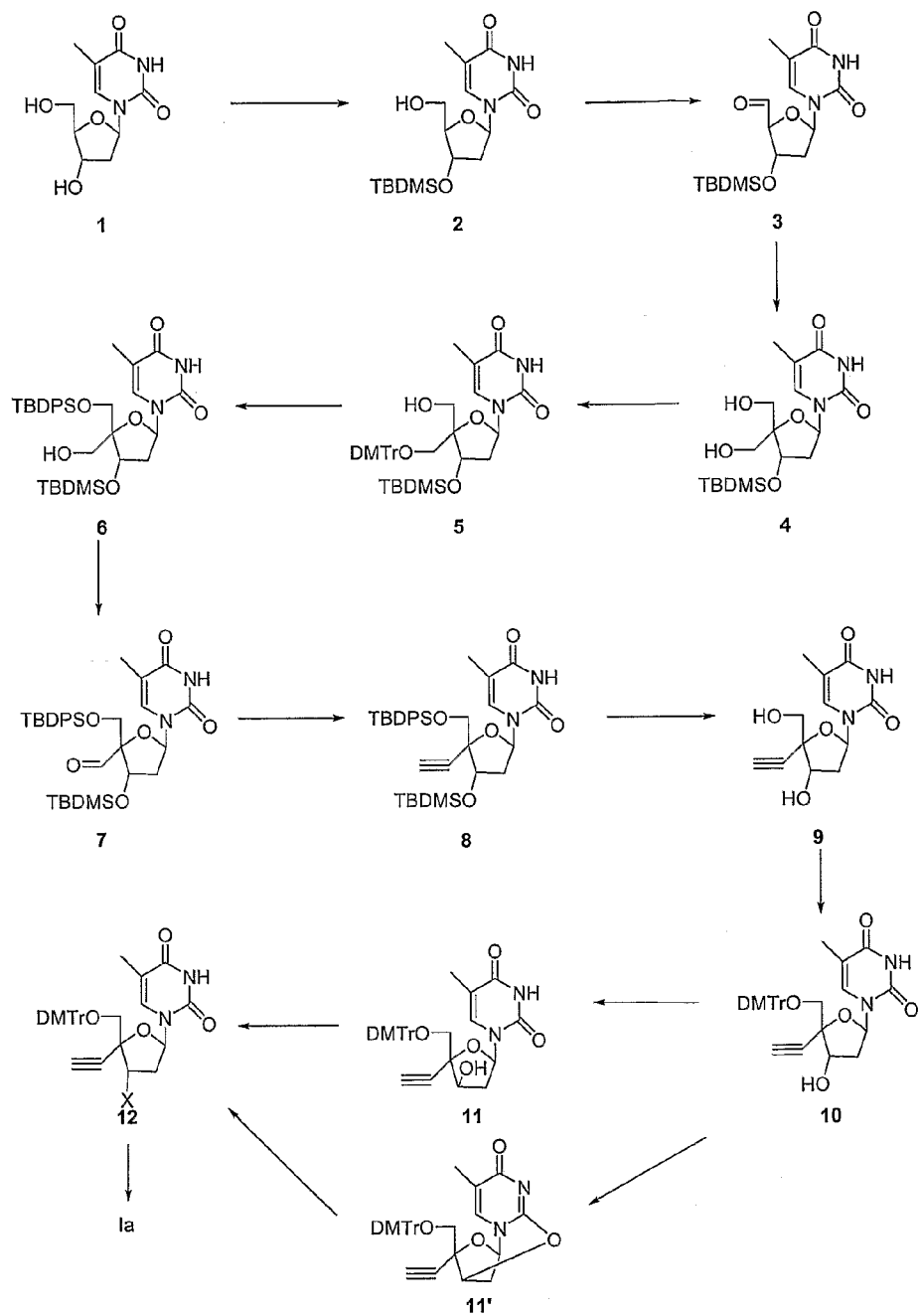
FIG. 2 is a nonlimiting illustrative example of the synthesis of 4'-C-ethynyl-3'-fluorothymidine (Ia, $R^1$=F, $R^2$=OH, $R^3$=ethynyl) or 4'-C-ethynyl-3'-azidothymidine (Ia, $R^1$=$N_3$, $R^2$=OH, $R^3$=ethynyl).

Preparation of 4'C-ethynyl-5'-O-(dimethoxytrityl) thymidine (10, FIG. 2)

To a solution of 4'-C-ethynylthymidine (1 mmol) in pyridine (10 ml) is added dimethoxytrityl chloride (1.2 mmol) at 0° C. and the resulting solution is stirred at room temperature for 3 h. EtOAc (100 mL) is added and the solution is washed with water and dried ($Na_2SO_4$). Solvent is evaporated to dryness under reduced pressure. The residue is co-evaporated with toluene (2×20 mL) and purified by silica gel column chromatography (5% MeOH in methylene chloride) to give 4'C-ethynyl-5'-O-(dimethoxytrityl)thylnidine (10).

Example 3

Preparation of 4'-C-ethynyl-5'-O-(dimethoxytrityl)-2,3'-anhydrothymidine (11', FIG. 2)

To a solution of 10 (1 mmol) in methylene chloride (20 mL) are added triethylamine (1 mL) and methanesulfonyl chloride (1.2 mmol) and the solution is stirred at room temperature for 16 h. EtOAc (50 mL) is added and the mixture is washed with water, and dried ($Na_2SO_4$). Solvent is removed and the residue is dissolved in anhydrous tetrahydrofuran (THF, 20 mL). To the solution is added DBU (3 mmol) and the resulting solution is refluxed for 16 h. The solution is diluted with EtOAc (50 mL) and washed with brine. Organic solution is dried ($Na_2SO_4$) and solvent is removed and the residue is purified by silica gel column chromatography (2% MeOH in methylene chloride) to provide compound 11'.

Example 4

Preparation of 4'-C-ethynyl-5'-O-(dimethoxytrityl)-3'-azido-3'-deoxythymidine (12, X=$N_3$, FIG. 2)

To a solution of 11' (1 mmol) in dry DMF (10 mL) is added $NaN_3$ (3 mmol) and the mixture is stirred at 100° C. for 16 h.

Solvent is evaporated to dryness under reduced pressure. The residue is co-evaporated with toluene (2×20 mL) and purified by silica gel column chromatography (20-50% EtOAc in hexanes) to afford 4'-C-ethynyl-5'-O-(dimethoxytrityl)-3'-azido-3'-deoxythymidine (12, X=$N_3$).

Example 5

Preparation of 4'-C-ethynyl-3'-azido-3'-deoxythymidine (Ia, X=$N_3$, FIG. 2)

A solution of 4'-C-ethynyl-5'-O-(dimethoxytrityl)-3'-azido-3'-deoxythymidine (12, X=$N_3$) (1 mmol) in a solution of 1% trifluoroacetic acid in methylene chloride (20 mL) is stirred at room temperature for 3 h and neutralized with ammonium hydroxide. Solvent is evaporated to dryness under reduced pressure and the residue is purified by silica gel column chromatography (2-5% MeOH in methylene chloride) to give 4'-C-ethynyl-AZT (Ia, X=$N_3$).

Example 6

Preparation of 4'-C-ethynyl-5'-O-(dimethoxytrityl)-3'-fluoro-3'-deoxythymidine (12, X=F, FIG. 2)

To a solution of 11' (1 mmol) in dry DMF (10 mL) is added tetrabutylammonium fluoride (TBAF, 3 mmol) and the mixture is stirred at 100° C. for 16 h. Solvent is evaporated to dryness under reduced pressure. The residue is co-evaporated with toluene (2×20 mL) and purified by silica gel column chromatography (20-50% EtOAc in hexanes) to afford 4'-C-ethynyl-5'-β-(dimethoxytrityl)-3'-fluoro-3'-deoxythymidine (12, X=F).

Example 7

Preparation of 4'-C-ethynyl-3'-fluoro-3'-deoxythymidine (Ia, X=F, FIG. 2)

A solution of 4'-C-ethynyl-5'-O-(dimethoxytrityl)-3'-fluoro-3'-deoxythymidine (12, X=F) (1 mmol) in a solution of 1% trifluoroacetic acid in methylene chloride (20 mL) is stirred at room temperature for 3 h and neutralized with ammonium hydroxide. Solvent is evaporated to dryness under reduced pressure and the residue is purified by silica gel column chromatography (2-5% MeOH in methylene chloride) to give 4'-C-ethynyl-FLT (Ia, X=F).

Anti-HIV Activity

Example 8

MTT Method Using MT-4 Cells

A test agent (100 μL) is diluted on a 96-well microplate. MT-4 cells infected with HIV-1 ($III_b$ strain; 100 $TCID_{50}$) and non-infected MT-4 cells are added to the microplate such that the number of cells in each well becomes 10,000. The cells are cultured at 37° C. for five days. MTT (20 μL 7.5 mg/ml) is added to each well, and the cells are further cultured for 2-3 hours. The cultured medium (120 μL) is sampled, and MTT terminating solution (isopropanol containing 4% Triton X-100 and 0.04N HCl) is added to the sample. The mixture is stirred to form formazane, which is dissolved. The absorbance at 540 nm of the solution is measured. Since the absorbance is proportional to the number of viable cells, the test agent concentration at which a half value of the absorbance is measured in a test using infected MT-4 cells represents $EC_{50}$, whereas the test agent concentration at which a half value of the absorbance is measured in a test using non-infected MT-4 cells represents $CC_{50}$.

Example 9

MAGI Assay Using HeLa CD4/LTR-beta-Gal Cells

HeLa CD4/LTR-beta-Gal cells are added to 96 wells such that the number of cells in each well is 10,000. After 12-24 hours, the culture medium is removed, and a diluted test agent (100 μL) is added. A variety of HIV strains (wild strain: WT, drug-resistant strain: MDR, M184V, NL4-3, 104pre, and C; each equivalent to 50 $TCID_{50}$) are added, and the cells are further cultured for 48 hours. The cells are fixed for five minutes using PBS containing 1% formaldehyde and 0.2% glutaraldehyde. After the fixed cells are washed with PBS three times, the cells are stained with 0.4 mg/ml X-Gal for one hour, and the number of blue-stained cells of each well is counted under a transmission stereoscopic microscope. The test agent concentration at which blue-stained cells decreases to 50% and 90% in number represented $EC_{50}$ and $EC_{90}$, respectively. In a manner similar to that employed in the MTT method, cytotoxicity is measured by use of HeLa CD4/LTR-beta-Gal cells.

Anti-HBV Activity

Example 10

Anti-HBV AD38 Assay

A HepG2-AD38 cell line is established in a culture medium that comprised DMEM-F/12, 10% fetal bovine serum, 100 IU/mL/100 μg/mL of penicillin/streptomycin, 50 μg/mL kanamycin, 0.3 μg/mL tetracycline, and 200 μg/mL G418. The assay medium for the HepG2-AD38 cell line comprises RPMI-1640, 10% fetal bovine serum, 100 IU/mL/ 100 μg/mL of penicillin/streptomycin, 50 μg/mL kanamycin, and 200 μg/mL G418. Other materials utilized for this assay are as follows: phosphate buffered saline (PBS), biocoated 96 well plates, DNeasy 96 tissue kit (Qiagen), QIAvac 96 vacuum manifold, Micro amp optical 96 well reaction plates (Applied Biosystems), Micro amp optical caps (Applied Biosystems), Taqman Universal PCR Master Mix (Applied Biosystems), 7700 Sequence detector (Applied Biosystems), and primers and probe for HBV DNA: 1125 nM forward primer (primer 1), GGA CCC CTG CTC GTG TTA CA (SEQ ID NO:1); 1125 nM reverse primer (primer 2), GAG AGA AGT CCA CCA CGA GTC TAG A (SEQ ID NO:2); and 250 nM probe, FAM-TGT TGA CAA GAA TCC TCA CAA TAC CAC (SEQ ID NO:3).

Methodology

Cell Assay.

Wells of a 96-well biocated plate are seeded with the appropriate amount of cells, such as 5×$10^4$ cells/well, and are incubated at 37° C. with 5% $CO_2$. After 2 days, the supernatant is carefully removed, and the cell layer is washed with PBS, and is subsequently renewed with assay medium with or without test compounds in an appropriate amount (such as 10 μM or in a dose response with a ratio of 1:3 starting at 10 μM. Samples are tested in duplicate. Cells are allowed to grow for 5 more days, in which at day 7, an amount of supernatant, such as 180 μL, is collected and stored in an appropriate container (such as in a blue rack included in the DNeasy 96 tissue kit either at −80° C. or room temperature depending upon whether or not the extraction step is to be performed immediately or at sometime afterwards.

Extraction of Viral HBV DNA from Cell Supernatant.

The supernatant samples collected at day 7 are either thawed or used as is. A Proteinase K/Buffer ATL working solution, which comprises 2 mL of Proteinase K and 18 mL of Buffer ATL, is transferred on the top of the supernatant samples. The tubes are then sealed and mixed by repeated inversion. The tubes are then centrifuged, up to 3000 rpm, in order to collect any solution from the caps, which are subsequently used and referred to as the cap solution. The tubes are incubated at 55° C. for 15 minutes, and then are centrifuged up to 3000 rpm again. To each sample is added 410 μL of Buffer AL/E. The tubes are sealed anew, placed in a rack, and shaken vigorously for an appropriate amount of time (such as, 15 seconds), and the tubes are then centrifuged up to 3000 rpm. At this point the DNeasy 96 plate is placed on top of QIAvac 96 vacuum manifold. The cap solution is then transferred to the DNeasy 96 plate, and vacuum is applied for an appropriate amount of time. An amount of Buffer AW1 (such as 500 μl) is added to each well, and then vacuum is applied again for an appropriate amount of time (such as about 1 minute). To the wells is added an amount of Buffer AW2 (such as 500 μL), and vacuum is applied again for an amount of time (such as 1 minute). The solution contents in the wells is then agitated, and then vacuum is applied again for an amount of time (such as 10 minutes). The DNA is eluted by adding pre-heated Buffer AE to each well and subsequently adding vacuum.

Real Time PCR.

Real Time PCR.

It is necessary to prepare sufficient HBV primers and probe solution for 200 wells (total 1500 μL) by employing the following solution that comprises 100 μM of primer 1, 100 μM of primer 2, 50 μM of probe in nuclease free water. It is also necessary to prepare a sufficient amount of a reaction mixture that comprises Universal PCR Master Mix, the HBV primers and probe solution, and nuclease free water. To each well of an optical 96 well reaction plate is added an appropriate amount of the reaction mixture and HBV DNA from each sample. The wells are covered with optical caps and then they are centrifuged for the appropriate amount of time. The plate is placed in a sequence detector (such as a 7700 Sequence detector), and the reporter is selected for FAM, and the volume setting is selected for 25 μL. The machine is started and after a certain period of time (about 2 hrs.), the dCt and reduction in viral load is calculated for each test compound.

Example 11

8 Day Cytotoxicity Assay

HepG2 (liver)BxPC3 (pancreatic) and CEM (Lymphocytic) cell lines are established in appropriate culture media. For example, the culture media for the HepG2 cell line comprises DMEM, 10% fetal bovine serum, and 100 IU/mL/100 μg/mL of Penicillin/streptomycin. The assay media for BxPC3 and CEM comprises RPMI-1640, 10% fetal bovine serum, and 100 IU/mL/100 μg/mL of penicillin/streptomycin.

Methodology.

An amount of 2× drug dilutions are added to the wells of a 96-well plate. 50 μL of 2× drug dilutions is added in a 96 well plate. In every assay, a "no drug" (medium only) control is used to determine the minimum absorbance values and a "cells+medium only" control is used for the maximum absorbance value. A solvent control is also used if the drug is dissolved in DMSO. The cells are counted and resuspended in the appropriate assay medium. It is noted that the cells should be added at 2000 cells per well. New cell suspensions are added to each well and the plate is incubated at 37° C. with 5% $CO_2$ for 8 days. After 8 days of incubation, MTS dye is added to each well and the plate is incubated for 2 hours at 37° C. with 5% $CO_2$. The plates are then read using an ELISA plate reader at a wavelength of 490 nm. The absorbance of the medium-only control wells is calculated. The 50% inhibition value ($CC_{50}$) is determined by comparing the absorbance in the no-drug cell control wells with the absorbance in wells containing cells and test drug.

---

We claim:

1. A compound which is a β-D- and β-L-nucleoside or a pharmaceutically acceptable salt thereof, having a structure defined by formula (I) or by formula (II):

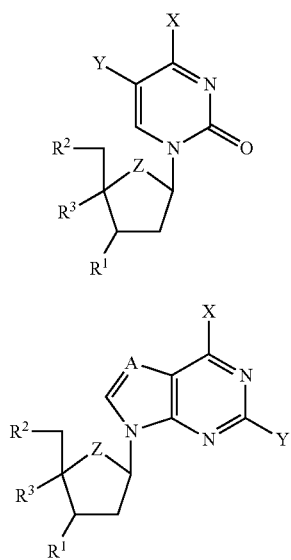

wherein:

X is hydrogen, F, Cl, Br, I, $NH_2$, $NHR^4$, $NR^4R^5$, NHOH, $NHOR^4$, $NHNH_2$, $NR^4NH_2$, $NHNHR^4$, SH, $SR^4$, $S(O)_b R^4$, OH, $OR^4$, $N_3$, CN, or $CF_3$;

Y is hydrogen, F, Cl, Br, I, $NH_2$, $NHR^4$, $NR^4R^5$, NHOH, $NHOR^4$, $NHNH_2$, $NR^4NH_2$, $NHNHR^4$, SH, $SR^4$, $S(O)_b$ $R^4$, OH, $OR^4$, $N_3$, CN, $CF_3$, hydroxymethyl, methyl, substituted or unsubstituted ethyl, substituted or unsubstituted vinyl, substituted or unsubstituted 2-bromovinyl, or substituted or unsubstituted ethynyl;

$R^1$ is F or $N_3$;

$R^2$ is OH, $OR^4$, $OC(O)R^4$, $-OP(O)(OQ)_a(NHR^4)_b$, SH, $SR^4$, $S(O)_b R^4$, $SC(O)R^4$, $NH_2$, $NHC(O)R^4$, $NHR^4$, $NR^4R^5$, NHOH, $NHOR^4$, NHNH, $NR^4NH_2$, or $NHNHR^4$;

$R^3$ is F, cyano, azido, ethynyl, chlorovinyl, fluorovinyl, alkyl ($C_{2-6}$), one to three halogen substituted alkyl ($C_{1-6}$), alkenyl or alkynyl ($C_{2-6}$);

Z is O, S, $CH_2$ or $C=CH_2$;

A is N, CH, or CF; and $R^4$ and $R^5$ are the same or different and are lower alkyl, lower alkenyl, acyl of carbon 1-17, aryl, or aralkyl;

M is at least one member selected from the group consisting of $H^+$, $Na^+$, and $K^+$;

and a has a value of 0 or 1, b has a value of 1 or 2, and Q is M or $R^4$.

2. The compound of claim 1, wherein the nucleoside is a 4'-C-substituted-3'-fluoro-2',3'-dideoxynucleoside.

3. The compound of claim 1, wherein the nucleoside is a 4'-C-substituted-3'-azido-2',3'-dideoxynucleoside.

4. The compound of claim 1, wherein the nucleoside is a 4'-C-ethynyl-3'-fluoro-2',3'-dideoxynucleoside.

5. The compound of claim 1, wherein the nucleoside is a 4'-C-ethynyl-3'-azido-2',3'-dideoxynucleoside.

6. The compound of claim 1, wherein the nucleoside is a 4'-C-ethynyl-3'-fluoro-3'-deoxythymidine.

7. The compound of claim 1, wherein the nucleoside is a 4'-C-ethynyl-3'-azido-3'-deoxythimidine.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
ggacccctgc tcgtgttaca                                           20

<210> SEQ ID NO 2
<211> LENGTH: 25
<212> TYPE: DNA
<213> ORGANISM: Artificial Sequence
<220> FEATURE:
<223> OTHER INFORMATION: Reverse primer

<400> SEQUENCE: 2
gagagaagtc caccacgagt ctaga                                     25

```
<210> SEQ ID NO 3
<211> LENGTH: 27
<212> TYPE: DNA
<213> ORGANISM: Artificial Sequence
<220> FEATURE:
<223> OTHER INFORMATION: FAM-labeled probe

<400> SEQUENCE: 3
tgttgacaag aatcctcaca ataccac                                              27
```